Sept. 6, 1938. L. BURBANK Plant Pat. 290
PEACH TREE
Filed Dec. 15, 1937
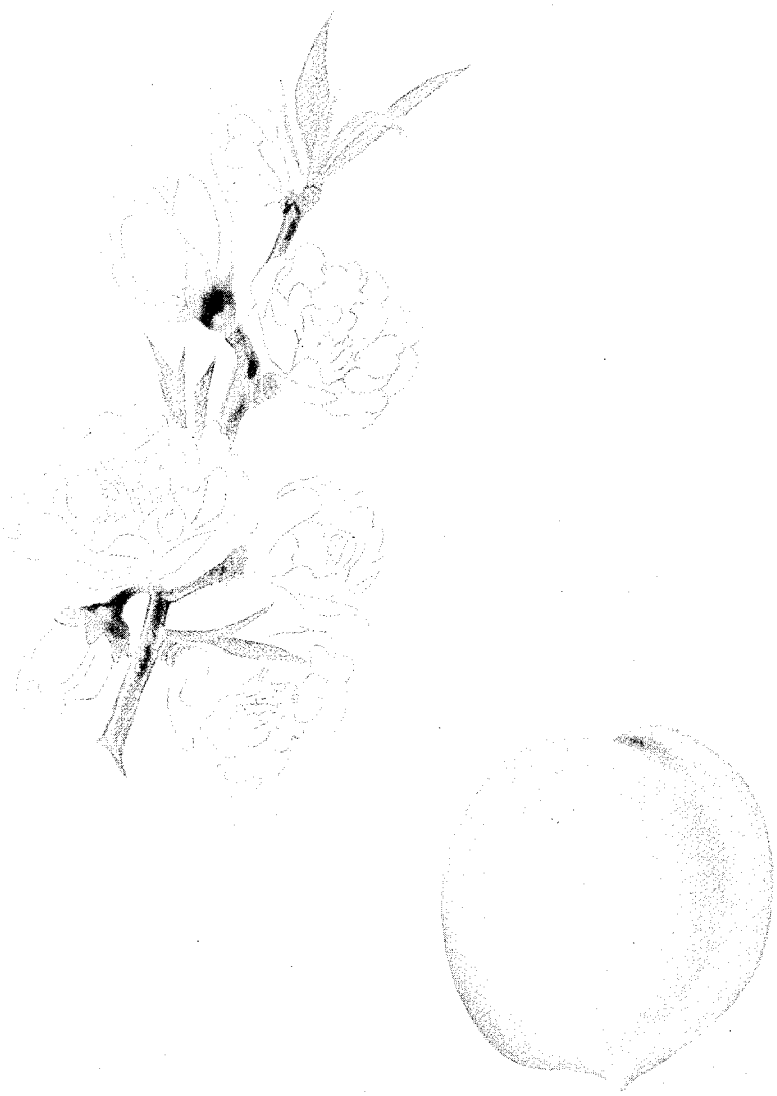
Inventor
Luther Burbank
By Elizabeth Waters Burbank
Executrix of the Estate of
Luther Burbank, deceased
By Robb & Robb
Attorneys Patented Sept. 6, 1938

Plant Pat. 290

UNITED STATES PATENT OFFICE

290

PEACH TREE

Luther Burbank, deceased, late of Santa Rosa, Calif., by Elizabeth Waters Burbank, executrix, Santa Rosa, Calif., assignor to Stark Bro's Nurseries & Orchards Company, Louisiana, Mo.

Application December 15, 1937, Serial No. 180,042

1 Claim. (Cl. 47—62)

The present invention relates to a new and distinct variety of peach tree of the pink double flowering type, the primary novel characteristic of which resides in the edibility of its fruit.

Double-flowering peach trees have been known and cultivated for many years in China and Japan. These trees are slender and willow-like, generally with drooping branches and small double blossoms produced in profusion. The flowers are usually one-quarter inch in diameter. The fruit of these peach trees, however, is not edible, even when cooked.

It is an object of the present invention to provide a new variety of peach tree of this double-flowering type bearing large size double flowers and edible fruit, and the new variety is the result of crosses between the Japanese and Chinese double-flowering peach varieties and other standard peaches of high quality with the definite effort to improve both the flowers and the fruit.

The blossoms of this new peach are very large in size, averaging from $2\frac{1}{16}$ to $2\frac{1}{4}$ inches in diameter, and are borne in profusion before the leaves appear. The coloring of the blossoms is a beautiful clear pink which has proven to fade less than other varieties under test. The flowers are rose-like in appearance, the petals averaging from about 20 to 25 in number.

The fruit is of a very good quality. The flesh is very tender and juicy and presents a pleasing spicy aroma. The peach very closely resembles that of the Stark Summer Heath in appearance and size, the new variety being of the freestone type, however, whereas the Stark Summer Heath is a cling.

The tree is strong growing and hardy.

Asexual reproduction has proven the new variety to reproduce true to form.

The following is a detail description:—

Tree:

Hardy, strong growing.

Flower:

Flower is large in size, approximately $2\frac{1}{16}$ to $2\frac{1}{4}$ inches in diameter.

*Blooming season.*—Mid-season.

*Flower stems.*—Short, not often over $\frac{1}{8}$ inch long; rather stout; green with shading of the calyx color.

*Calyx.*—Large, cup-shape with large lobes concave and lying in close contact with the outer petals. Body of calyx glossy, with surface minutely wrinkled, as also the calyx lobes, which are grayish pubescent toward the tips and along the edges. Color.—Victoria lake*.

*Flower buds.*—Develop to globular form, or obovate when considered with the calyx. Color—Tyrian pink*, the small outer petals a shade deeper than the next row.

*Open flower.*—Petals—20 to 25, generally rounded in outline, but showing a distinct short petiole, and so arranged in five groups that five openings may be seen to extend to the calyx. Margins of petals wavy and occasionally notched, but usually entire. Some of inner petals much smaller, a few deformed and showing partial stamen structures. Color—Rose pink*.

*Stamens.*—40 to 50, often distinctly shorter than the petals. Filaments white when first exposed, usually the same color as the petals, but sometimes shading to a much darker color on older flowers.

*Anthers.*—Rather small. Color—Morocco red*.

*Pistil.*—As long as the stamens, style white. Pistil sometimes absent, and sometimes fully developed and even two in the same flower.

Fruit:

*Quality.*—Good.

*Season.*—Mature to commercial picking stage about August 15th; ripe for best flavor August 22nd; extreme range about August 28th, at Santa Rosa, California.

*Size.*—Medium to small. Axial diameter—$2\frac{3}{8}$ inches; longest transverse diameter—$2\frac{1}{4}$ inches; shortest transverse diameter—$2\frac{1}{8}$ inches.

*Form.*—Globular, inclined to broad ovate, this appearance enhanced by a tendency to develop a pointed apex on some specimens. Contour unsymmetrical in most specimens, the portion including the suture always the smaller.

*Stem.*—Very short, small, separating readily from the fruit when ripe. Base of fruit relatively broad and flattened.

*Cavity.*—Wide, deep; oval in cross-section.

*Suture.*—Indenting the small end of oval rather deeply and continuing as a shallow furrow to the apex, scarcely noticeable in some specimens.

*Apex.*—Rounded to prominent, with small brown dry point.

*Surface.*—Smoothly rounded, covered with short thickly set white pubescence. Color—pale cream or Naples yellow when mature, shaded mostly from the cavity outward with soft rose pink over one-eighth to one-fourth of the surface area, mostly deeply shaded on the sides of the cavity.

*Skin.*—Thin, fairly tough; not easily removed.

*Flesh.*—Tender, juicy, fine textured; slightly fibrous, scarcely adhering to stone. Color—white with creamy tinge, marbled with bright rose pink near the stone. Flavor—sub-acid to sweet, slightly astringent, and with a pleasing spicy aroma.

*Ridgway's Color Standard.

*Ridgway's Color Standard.

*Stone.*—Free, rounded ovate with unequal sides and a prominent sharp point. Size medium for size of fruit. 1⅛ inches long to extreme point of apex; ⅞ inch wide; ¾ inch thick. Convolutions numerous and fairly deep. Suture ridges prominent. Color — warm brown with faint tinge of rose pink near sutures.

The tree has produced light to medium crops of fruit during the years of observation.

What is claimed is:

A new and distinct variety of double-flowering peach tree which produces large double blossoms of a clear pink color that do not readily fade, and edible fruit, substantially as shown and described.

ELIZABETH WATERS BURBANK,
*Executrix of the Estate of Luther Burbank, Deceased.*